US010421611B2

(12) United States Patent
Kwon et al.

(10) Patent No.: US 10,421,611 B2
(45) Date of Patent: Sep. 24, 2019

(54) GEOLOGICAL STORAGE SYSTEM OF CARBON DIOXIDE AND PROCESS FOR GEOLOGICAL STORAGE OF CARBON DIOXIDE

(71) Applicant: KOREA ADVANCED INSTITUTE OF SCIENCE AND TECHNOLOGY, Daejeon (KR)

(72) Inventors: Tae-Hyuk Kwon, Daejeon (KR); Taehyung Park, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/052,781

(22) Filed: Aug. 2, 2018

(65) Prior Publication Data

US 2019/0062059 A1 Feb. 28, 2019

(30) Foreign Application Priority Data

Aug. 25, 2017 (KR) .................. 10-2017-0107819

(51) Int. Cl.
*B65G 5/00* (2006.01)
*C07K 7/06* (2006.01)
*E21B 41/00* (2006.01)

(52) U.S. Cl.
CPC ............... *B65G 5/005* (2013.01); *C07K 7/06* (2013.01); *E21B 41/0064* (2013.01)

(58) Field of Classification Search
CPC ....... B65G 5/00; B65G 5/005; E21B 41/0057; E21B 41/0064
See application file for complete search history.

(56) References Cited

U.S. PATENT DOCUMENTS

| 8,646,538 | B2 * | 2/2014 | Baxter | B01D 53/62 166/402 |
| 2011/0013986 | A1 * | 1/2011 | Zebrowski | C09K 8/582 166/246 |
| 2011/0056373 | A1 * | 3/2011 | Baxter | B01D 53/62 95/213 |
| 2011/0067856 | A1 * | 3/2011 | Kohr | C09K 8/582 166/246 |

(Continued)

FOREIGN PATENT DOCUMENTS

| CA | 2804097 | * | 1/2012 | ............ E21B 41/00 |
| CA | 2807194 A1 | * | 2/2012 | ......... E21B 41/0035 |

(Continued)

OTHER PUBLICATIONS

Taehyung Park et al., "Biosurfactant as an Enhancer of Geologic Carbon Storage: Microbial Modification of Interfacial Tension and Contact Angle in Carbon dioxide/Water/Quartz Systems", Frontiers in Microbiology, vol. 8. Article 1285, Jul. 2017.

(Continued)

*Primary Examiner* — Frederick L Lagman
(74) *Attorney, Agent, or Firm* — Lex IP Meister, PLLC

(57) ABSTRACT

A geological storage system of carbon dioxide according to an exemplary embodiment of the present invention includes: an injection pipe that extends to a carbon storage reservoir that includes a plurality of rock grains and brine, from the ground surface, and supplies an injection material that includes carbon dioxide ($CO_2$) to the carbon storage reservoir; a plurality of pores that are disposed between the plurality of rock grains; and a storage structure that is connected with a part of the plurality of pores and where the carbon dioxide reaches through the plurality of pores and then stored.

10 Claims, 7 Drawing Sheets

(56) References Cited

U.S. PATENT DOCUMENTS

| | | | | |
|---|---|---|---|---|
| 2011/0139455 | A1* | 6/2011 | Kameyama | E21B 41/0064 166/305.1 |
| 2012/0038174 | A1* | 2/2012 | Bryant | E21B 41/0064 290/1 R |
| 2012/0090325 | A1* | 4/2012 | Lewis | E21B 41/0064 60/772 |
| 2012/0103602 | A1* | 5/2012 | Lackner | B01F 5/0496 166/250.12 |
| 2012/0118586 | A1* | 5/2012 | Kameyama | E21B 41/0064 166/401 |
| 2014/0174739 | A1* | 6/2014 | Bourcier | C09K 8/5045 166/292 |

FOREIGN PATENT DOCUMENTS

| | | | | |
|---|---|---|---|---|
| CA | 2812470 | A1 * | 4/2012 | ......... E21B 41/0064 |
| CA | 2839701 | A1 * | 1/2013 | ......... E21B 41/0064 |
| CN | 104533361 | * | 4/2015 | ......... E21B 41/0057 |
| KR | 10-2010-0068088 | | 6/2010 | |
| KR | 10-2011-0012588 | | 2/2011 | |
| KR | 10-2012-0096692 | | 8/2012 | |
| KR | 10-1443883 | | 9/2014 | |
| KR | 10-1586687 | | 1/2016 | |
| KR | 10-1591426 | | 2/2016 | |
| WO | WO 2010/145676 | * | 12/2010 | ............... C09K 8/52 |

OTHER PUBLICATIONS

Kim, S., & Santamarina, J. C., "Engineered $CO_2$ injection: The use of surfactants for enhanced sweep efficiency", International Journal of Greenhouse Gas Control, 20, 324-332, Jan. 2014.

Khire, J. M., "Bacterial biosurfactants, and their role in microbial enhanced oil recovery (MEOR)", Biosurfactants, pp. 146-157, Springer New York, 2010.

* cited by examiner

GEOLOGICAL STORAGE SYSTEM OF CARBON DIOXIDE AND PROCESS FOR GEOLOGICAL STORAGE OF CARBON DIOXIDE

CROSS-REFERENCE TO RELATED APPLICATION

This application claims priority to and the benefit of Korean Patent Application No. 10-2017-0107819 filed in the Korean Intellectual Property Office on Aug. 25, 2017, the entire contents of which are incorporated herein by reference.

BACKGROUND OF THE INVENTION (a) Field of the Invention

The present invention relates to a geological storage system of carbon dioxide and a method for geologically storing carbon dioxide.

(b) Description of the Related Art

As a method for massively reducing greenhouse gasses to alleviate global warming, interest and demand for a carbon dioxide capture and storage (CCS) method have increased.

A technology for trapping and storing carbon dioxide refers to a technology for long-term storing and managing of carbon dioxide trapped from large-scale sources of carbon dioxide such as power plants and steel mills to correspond to demand for greenhouse gas reduction because of climate change and under the Kyoto Protocol, in coal seams, reservoirs such as petroleum and gas fields, a saline aquifer, and the like.

However, when the carbon dioxide is stored in the saline aquifer, it may not be easy to control the behavior of carbon dioxide due to a capillary phenomenon occurring in pores disposed in the saline aquifer.

In order to increase the storage of carbon dioxide by controlling the behavior of carbon dioxide, an acid gas may be injected to change interface properties of the carbon dioxide and brine, but such a method may not be economical and may cause environmental problems.

In addition, although there is a method of pouring brine of the saline aquifer into the saline aquifer as a gas-liquid mixed fluid by saturating the carbon dioxide into micro-bubbles, water pumps or other pumps may be needed to pump up brine, the scale of the system may become too large, and energy consumption for storage may become excessive.

The above information disclosed in this Background section is only for enhancement of understanding of the background of the invention and therefore it may contain information that does not form the prior art that is already known in this country to a person of ordinary skill in the art.

SUMMARY OF THE INVENTION

An exemplary embodiment of the present invention has been made in an effort to provide a system for geologically storing carbon dioxide, and a method for geologically storing carbon dioxide to reduce interfacial tension between brine and carbon dioxide.

A geological storage system of carbon dioxide according to an exemplary embodiment of the present invention, and a method for geologically storing carbon dioxide are provided to increase a contact angle between brine, carbon dioxide, and rocks.

A geological storage system of carbon dioxide according to an exemplary embodiment of the present invention, and a method for geologically storing carbon dioxide are provided to reduce a capillary pressure.

A geological storage system of carbon dioxide according to an exemplary embodiment of the present invention, and a method for geologically storing carbon dioxide are provided to increase sweep efficiency of carbon dioxide in an carbon storage reservoir.

A geological storage system of carbon dioxide according to an exemplary embodiment of the present invention, and a method for geologically storing carbon dioxide are provided to in case a storage amount of carbon dioxide in the carbon storage reservoir.

The present invention can be used to achieve other efforts which are not described in detail in addition to the efforts.

A geological storage system of carbon dioxide according to an exemplary embodiment of the present invention includes: an injection pipe that extends to a carbon storage reservoir that includes a plurality of rock grains and brine, from the ground surface, and supplies an injection material that includes carbon dioxide ($CO_2$) to the carbon storage reservoir; a plurality of pores that are disposed between the plurality of rock grains; and a storage structure that is connected with a part of the plurality of pores and where the carbon dioxide reaches through the plurality of pores and then stored.

The plurality of pores and the storage structure may be filled with the brine, and the carbon dioxide may be separated from the brine by being surrounded by biosurfactants produced by microorganisms included in the injection material.

The carbon dioxide may be in a gas state, a liquid state, or a supercritical state.

The microorganism may be *Bacillus subtilis*, and the biosurfactant may be surfactin.

The biosurfactants may form a micelle structure, and the carbon dioxide may be trapped in the micelle structure.

Cap rocks may be disposed in upper and lower portions of the storage structure.

A method for geologically storing carbon dioxide according to an exemplary embodiment of the present invention includes: supplying an injection material that includes carbon dioxide ($CO_2$), microorganisms, and a bacterial growth medium through an injection pipe that extends to a carbon storage reservoir that includes a plurality of rock grains and brine, from the ground surface; forming a micelle structure by biosurfactants produced by the microorganisms, and forming a storage material by trapping the carbon dioxide in the micelle structure; moving the storage material through a plurality of pores that are disposed between the plurality of rock grains and filled with the brine; and storing the storage material by moving the storage material to a storage structure that is partially connected with the plurality of pores and filled with the brine.

Before the supply of the injection material to the carbon storage reservoir, a phase of the carbon dioxide may be converted to a liquid state or a supercritical state by using a phase conversion device.

The phase of the carbon dioxide may be determined corresponding to a temperature and a pressure environment of the carbon storage reservoir.

The microorganism may be *Bacillus subtilis*, and the biosurfactant may be surfactin.

In the supplying of the injection material to the carbon storage reservoir, an injection temperature, an injection pressure, and an injection amount of the injection material may be controlled.

According to the geological storing system of carbon dioxide and a method for geologically storing carbon dioxide according to exemplary embodiments of the present invention can reduce an interfacial tension between brine and carbon dioxide, increase a contact angle between brine, carbon dioxide, and rocks, reduce a capillary pressure, improve sweep efficiency of carbon dioxide in a carbon storage reservoir, and increase a storage amount of carbon dioxide.

DETAILED DESCRIPTION OF THE EMBODIMENTS

Figure 1:
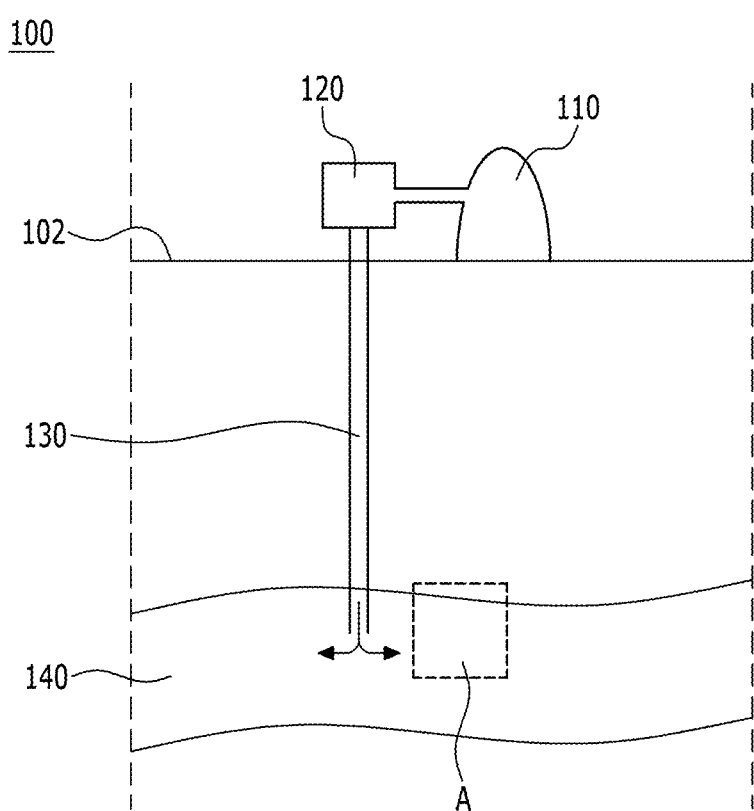
FIG. 1 schematically shows a cross-sectional view of a carbon dioxide geological storage system according to an exemplary embodiment.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification. In addition, in case of well-known technologies, a detailed description thereof will be omitted.

In the drawings, the thickness of layers, films, panels, regions, etc., are exaggerated for clarity. It will be understood that when an element such as a layer, film, region, or substrate is referred to as being "on" another element, it can be directly on the other element or intervening elements may also be present. Meanwhile, when an element is referred to as being "directly on" another element, there are no intervening elements present. In contrast, it will be understood that when an element such as a layer, film, region, or substrate is referred to as being "beneath" another element, it can be directly beneath the other element or intervening elements may also be present. Further, when an element is referred to as being "directly beneath" another element, there are no intervening elements present.

In addition, unless explicitly described to the contrary, the word "comprise" and variations such as "comprises" or "comprising" will be understood to imply the inclusion of stated elements but not the exclusion of any other elements.

FIG. 1 schematically shows a cross-sectional view of a carbon dioxide geological storage system according to an exemplary embodiment.

Referring to FIG. 1, a carbon dioxide geological storage system 100 includes a carbon dioxide ($CO_2$) storage tank 110, an injection portion 120, and an injection pipe 130 that is formed (extended or elongated) to an underground carbon storage reservoir 140 from the ground surface. Carbon dioxide stored in the carbon dioxide storage tank 110 is stored in the carbon storage reservoir 140 through the injection pipe 130 by the injection portion 120.

In embodiments, the carbon storage reservoir 140 may be a saline aquifer 140.

The saline aquifer 140 is a sedimentary layer saturated with stratum water or brine in which salts are dissolved at a high concentration, and includes an empty space existing between a plurality of grains, wherein the empty space is filled with brine. As a long-term saltwater-bearing geological structure, the saline aquifer 140 can safely store carbon dioxide without leakage, and since it is generally present in most regions of the world, the potential storage capacity of carbon dioxide can be large.

The saline aquifer 140 of the carbon dioxide geological storage system 100 according to the exemplary embodiment has a depth of about 800 m from the surface of the earth 102, but this is not restrictive. The depth of the saline aquifer 140 may be lower than about 800 m.

The carbon dioxide storage tank 110 that is disposed on the surface of the earth 102 may imply a facility where carbon dioxide collected from carbon dioxide production sites such as large-scale power generation facilities is transported and stored, and may be provided in plural. The collected carbon dioxide may be transported to the carbon dioxide storage tank 110 by using a pipe, a vessel, or a vehicle. The carbon dioxide storage tank 110 transmits carbon dioxide to the injection portion 120.

The injection portion 120 supplies an injection material that includes carbon dioxide, microorganisms, and a bacterial growth medium for microbial growth to the saline aquifer 140 through the injection pipe 130.

Here, the microorganisms may be, for example, *Bacillus subtilis* KCTC2189. A bacterial growth medium for growing *Bacillus subtilis* may include, for example, glucose, $MgSO_4$, $CaCl_2$, $FeSO_4$, $Na_2EDTA$, $MnSO_4$, $NH_4Cl$, $NaNO_3$, $KH_2PO_4$, $Na_2HPO_4$, and the like.

The *Bacillus subtilis* generates surfactin, which is a biosurfactant, while being grown in the above-stated culture solution. The surfactin includes a hydrophilic portion and a hydrophobic portion, and the hydrophilic portion is oriented toward the brine, thereby forming a micelle structure. In this case, carbon dioxide is trapped in the micelle structure such that a storage material is formed.

The injection portion 120 may include a temperature controller (not shown) that controls a temperature of carbon dioxide by using a temperature sensor (not shown) and a heating device (not shown), a flow amount and pressure controller (not shown) that controls a flow amount (injection amount) and a pressure (injection pressure) of carbon dioxide, a phase conversion device (not shown) that converts a phase of carbon dioxide corresponding to a temperature and a pressure environment of the saline aquifer 140, and a divider (not shown) that divides microorganisms and the bacterial growth medium, and thus a temperature, a flow amount, a flow pressure of carbon dioxide injected to the injection pipe 130, and an injection ratio of microorganisms and the culture solution can be controlled according to conditions.

Although it is not illustrated, distribution or density of rock grains around the outlet of the injection pipe 130 may be low, and there may be no cap rock (an impervious layer) that does not allow salt water and carbon dioxide to pass through, such as clayey rock. Accordingly, the storage material can be smoothly injected into the saline aquifer 140.

Carbon dioxide discharged through the outlet may reach a storage structure through an empty space (pores) between rock grains and then may be stored therein, and the storage structure may be pre-irradiated.

In this case, since the surfactin surrounds carbon dioxide and thus the micelle structure is formed, interfacial tension between the brine and carbon dioxide is reduced, and a contact angle may be increased and thus a capillary pressure may be reduced, and accordingly, fluidity or sweep efficiency of carbon dioxide may be improved and a stored amount or storage efficiency of carbon dioxide may be greatly increased. In addition, due to a structure of the storage material, carbon dioxide can be strategically injected to a stable storage structure.

Figure 2:
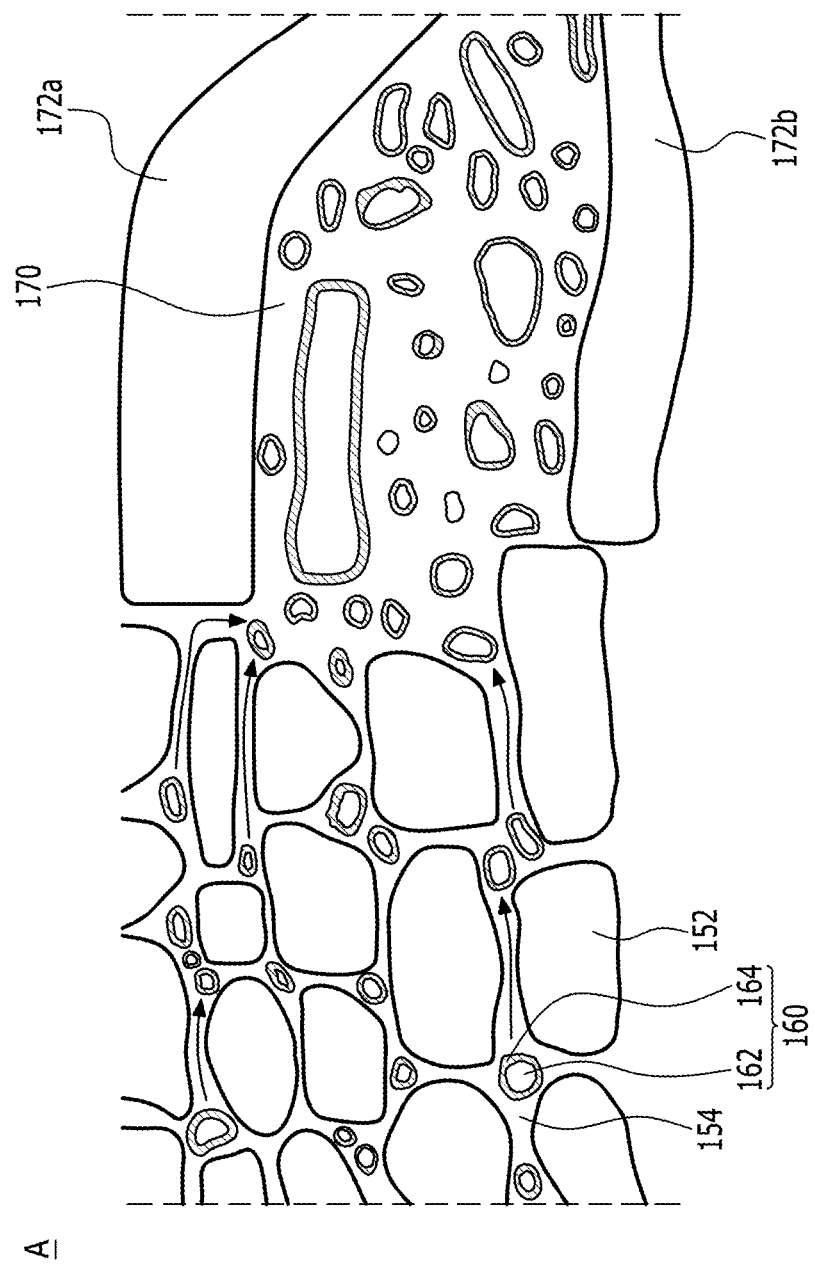
FIG. 2 shows the area A of FIG. 1 in detail.

FIG. 2 shows the area A shown as the dotted square area in FIG. 1 in detail.

Referring to FIG. 2, the carbon dioxide geological storage system 100 includes a plurality of pores 154 that are disposed between a plurality or rock grains 152, and a storage structure 170 that is connected with some of the plurality of pores 154 and where storage materials 160 that contain carbon dioxide 162 reach through the plurality of pores 154 and then stored.

In this case, the plurality of pores 154 and the storage structure 170 are filled with brine, and the carbon dioxide 162 discharged from the injection pipe 130 is surrounded by a biosurfactant 164, which is generated by microorganisms included in an injection material such that the storage materials 160 are formed, and accordingly, the carbon dioxide 162 may be separated (isolated) from brine.

The plurality of rock grains 152 of the saline aquifer 140 may be different from each other in size and shape, and thus the pores 154 may exist between every rock grain 152, and the storage material 160 may move along the pores 154.

In this case, as the intensity of the capillary pressure is low, the storage materials 160 can easily pass through the pores 154. The capillary pressure may also be expressed as a capillary breakthrough pressure. As the intensity of the capillary pressure is low, carbon dioxide is injected into the saline aquifer 140, effectively dispersed, and then stably stored in the storage structure 170. When sweep efficiency of carbon dioxide is deteriorated due to the capillary pressure, carbon dioxide cannot be moved to a desired place and a storage amount of carbon dioxide may be reduced.

The capillary pressure may imply a pressure difference of carbon dioxide and brine, and according to Equation 1, may be determined by the interfacial tension between the carbon dioxide 162 and the brine, a contact angle of the carbon dioxide 162 or the brine at the surface of the rock grain 152, and a radius of the pore 154.

$$P_c = P_{co_2} - P_w = \frac{2 \cdot \gamma_{w-CO_2} \cdot \cos\theta}{R} \quad \text{[Equation 1]}$$

In Equation 1, $P_C$ denotes a capillary pressure, $P_{CO2}$ denotes a pressure of carbon dioxide, $P_W$ denotes a pressure of brine, $\gamma_{W-CO2}$ denotes an interfacial tension between brine and carbon dioxide, and θ denotes a contact angle between brine—carbon dioxide—rock.

Here, the interfacial tension may imply force applied in a direction for reducing the area of an interface between brine and carbon dioxide when they contact each other. In addition, the contact angle between brine—carbon dioxide—rock implies a contact angle formed from contact between brine and contact between carbon dioxide and rock.

As the interfacial tension between brine and carbon dioxide is reduced, the capillary pressure may be reduced, and as the contact angle between brine—carbon dioxide—rock is increased, the capillary pressure may be reduced. As the capillary pressure is reduced, carbon dioxide can be strategically injected to the storage structure 170, and fluidity or sweep efficiency of carbon dioxide may be improved and a stored amount or storage efficiency of carbon dioxide may be greatly increased.

Compared to an existing system that solely injects carbon dioxide to the saline aquifer 140, the carbon dioxide geological storage system 100 according to the exemplary embodiment injects *Bacillus subtilis* and the culture solution thereof together with carbon dioxide, and thus the micelle structure is formed while the surfactin, which is a biosurfactant, generated by the *Bacillus subtilis* surrounds carbon dioxide 162, thereby forming the storage materials 160, and the interfacial tension between the brine and the carbon dioxide 162 can be reduced by the surfactin 164 and the contact angle between the brine—carbon dioxide—rock can be increased. Accordingly, the capillary pressure of the carbon dioxide 162 can be reduced, fluidity of the carbon dioxide 162 can be improved, and the storage amount of the carbon dioxide 162 can be increased.

The carbon dioxide 162 may be injected to the saline aquifer 140 in a gas state, a liquid state, or a supercritical state. Although it is not illustrated, carbon dioxide in a gas state may be changed to a liquid state or a supercritical state by the phase conversion device included in the injection portion 120.

The phase of the carbon dioxide 162 may be determined corresponding to a temperature and a pressure condition (environment) of the saline aquifer 140 where the saline aquifer 140 is to be stored.

For example, when the saline aquifer 140 in an environment of a high temperature and high pressure of about 31.48° 8 and about 7.4 MPa or higher, the carbon dioxide 162 in the gas state is changed to the supercritical state and then injected into the saline aquifer 140. In such a case, a depth of the saline aquifer 140 may be over about 800 m from the surface of the earth 102, and the carbon dioxide 162 may maintain the supercritical state, which enables the carbon dioxide 162 to have high density and high fluidity characteristics.

However, for example, when the depth of the saline aquifer 140 is less than 800 m from the surface of the earth 102 and the temperature/pressure conditions are not appropriate for the carbon dioxide 162 to maintain the supercritical state, the carbon dioxide 162 may be injected in the gas state or liquid state. When the carbon dioxide 162 needs to be injected in the liquid state, the phase conversion device (not shown) may perform phase conversion.

The saline aquifer 140 may be located with various depths from the surface of the earth 102, and the phase of the carbon dioxide 162 may be determined corresponding to a temperature and a pressure at each depth.

In order to store the storage materials 160, the saline aquifer 140 needs to be separated from a layer that can be used as drinking water. In addition, an area that is adjacent to the portion of the injection pipe 130, where the carbon dioxide 162 is injected to the saline aquifer 140, needs to assure sufficient porosity and permeability, and thus density of the rock grains 152 at the area may be relatively lower than that of other areas in the injection pipe 130.

The storage structure 170 where the storage material 160 reaches through the pores 154 may include an empty space that is significantly larger than the pore 154. The storage material 160 may be stored in the empty space in the storage structure 170. Compared to the conventional system, the fluidity of the storage materials 160 is enhanced by the biosurfactant 164, and thus a relatively much greater amount of storage materials 160 can reach the storage structure 170.

Cap rocks 172a and 172b may be disposed in upper and lower portions of the storage structure 170. In addition, the cap rocks 172a and 172b may be formed in at least a part of a side of the storage structure 170. The cap rocks 172a and 172b may be an impermeable layer through which brine and the storage material 160 cannot be permeated and thus the carbon dioxide 162 can be stored therein for a long period of time, and for example, may be clayey.

Hereinafter, a method for geologically storing carbon dioxide according to an exemplary embodiment will be described. Descriptions of the same components as those of the above-described components may be omitted.

A method for geologically storing carbon dioxide according to an exemplary embodiment includes supplying an injection material to a saline aquifer 140, forming a storage material 160, moving the storage material 160 through a plurality of pores 154, and storing the storage material 160 by moving the storage material 160 to the storage structure 170.

First, the injection material that includes carbon dioxide 162, microorganisms, and a bacterial growth medium is supplied to the saline aquifer 140 through the injection pipe 130 that extends to the saline aquifer 140.

In this case, before the injection material is supplied to the saline aquifer 140, a phase (gas, liquid, or supercritical) of the carbon dioxide 162 is determined by a phase conversion device (not shown), an injection ratio of the carbon dioxide 162, the microorganisms, and the bacterial growth medium can be determined in the injection portion 120, and an injection amount of the injection material, an injection temperature, and a pressure can be determined. The phase of the carbon dioxide 162 may be determined corresponding to a temperature and a pressure environment of the saline aquifer 140.

Next, a biosurfactant 164 generated by the microorganism forms a micelle structure, and the carbon dioxide 162 is trapped in the micelle structure such that the storage material 160 is formed.

Here, the microorganisms may be *Bacillus subtilis*, and an interfacial tension between brine and carbon dioxide is reduced and a contact angle between brine, carbon dioxide, and rocks can be increased by surf actin, which is the biosurfactant 164 generated by the *Bacillus subtilis*.

Next, the storage material 160 is moved through the plurality of pores 154, which are disposed between a plurality of rock grains 152 and filled with brine.

An injection pressure may be controlled in the injection portion 120 to move the storage material 160 to a predetermined storage structure 170, and sweep efficiency of the storage material 160 according to the exemplary embodiment can be remarkably superior to sweep efficiency of carbon dioxide in a conventional system.

Next, the storage material 160 is moved to the storage structure 170 that is partially connected with the plurality of pores 154 and filled with the brine to thereby store the storage material 160.

Hereinafter, the present invention will be described in more detail with reference to the following exemplary embodiment. However, the following exemplary embodiment is only illustrative of the present invention and the present invention is not limited thereto.

Figure 3:
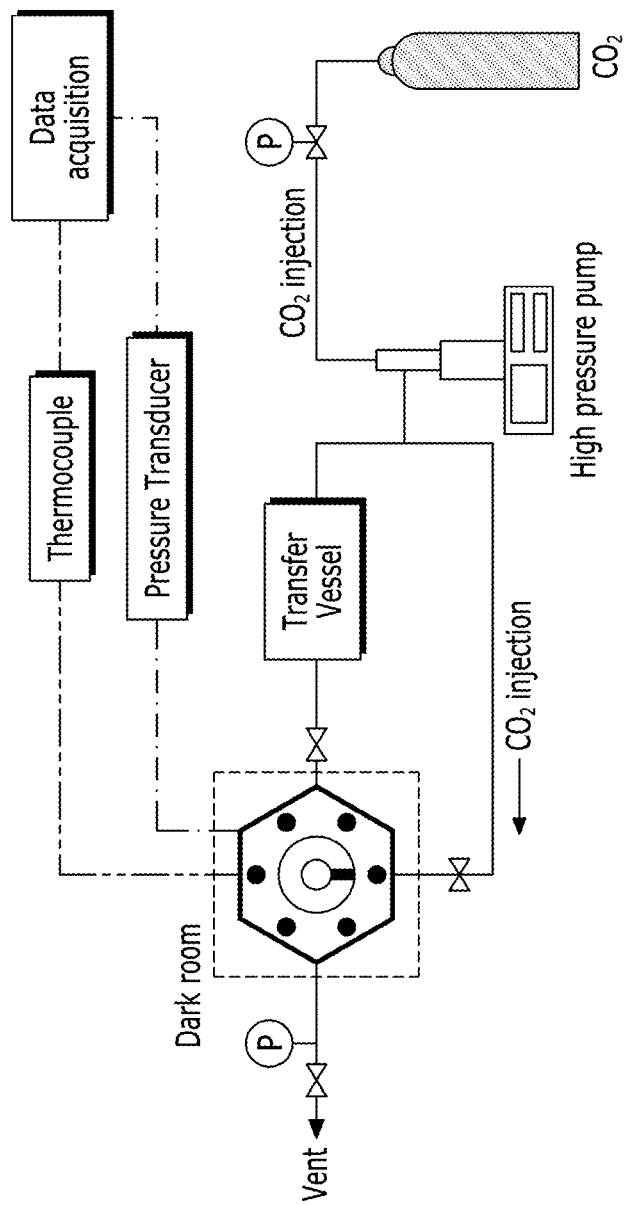
FIG. 3 is a schematic view of an experiment for measuring an interfacial tension variation and contact angle variation by surfactin.

FIG. 3 is a schematic view of an experiment for measuring an interfacial tension variation and contact angle variation by surfactin.

Referring to FIG. 3, in order to obtain an image having good quality, an interfacial tension variation and contact angle variation were carried out in a dark room, and an actual temperature of a saline aquifer 140 was implemented by winding a coil connected with a heat controller around a stainless reactor. In addition, carbon dioxide was injected to the reactor by using a high-pressure pump, and a pressure of the reactor was controlled by injecting a mixture of deionized water, *Bacillus subtilis*, and a culture solution through a transfer vessel. Such a pressure and temperature condition was monitored in real time through a pressure transducer and a thermocouple. The interfacial tension variation and the contact angle variation were measured by using a camera where a high-resolution macro lens is installed.

For the experiment, a temperature was set between about 301.15 K (28° 8) and about 310.15 K (37°( ), and a pressure was set between about 3 MPa and about 10 MPa for existence of carbon dioxide in a gas state, a liquid state, or a supercritical state. The experiment was carried with carbon dioxide existing in the gas state at about 310.15 K and about 3 MPa, carbon dioxide existing in the liquid state at about 301.15 K and about 10 MPa, and carbon dioxide existing in the supercritical state at about 310.15 K and about 10 MPa.

A capacity of the reactor was about 50 cm$^3$, and deionized water and carbon dioxide were used instead of salt water to reveal an independent effect of a temperature and a pressure.

Compounds of the culture solution used for the experiment are as shown in Table 1.

TABLE 1

| | Compound | Concentration |
| --- | --- | --- |
| Carbon source | Glucose | 40 g/L |
| Mineral salt medium | $MgSO_4$ | $8.0 \times 10^{-4}$M |
| | $CaCl_2$ | $8.0 \times 10^{-4}$M |
| | $FeSO_4$ | $8.0 \times 10^{-4}$M |
| | $Na_2EDTA$ | $8.0 \times 10^{-4}$M |
| | $MnSO_4$ | $8.0 \times 10^{-4}$M |
| Nitrogen source | $NH_4Cl$ | 0.1M |
| | $NaNO_3$ | 0.118M |
| Phosphate buffer | $KH_2PO_4$ | 0.03M |
| | $Na_2HPO_4$ | 0.04M |

Figure 4A:
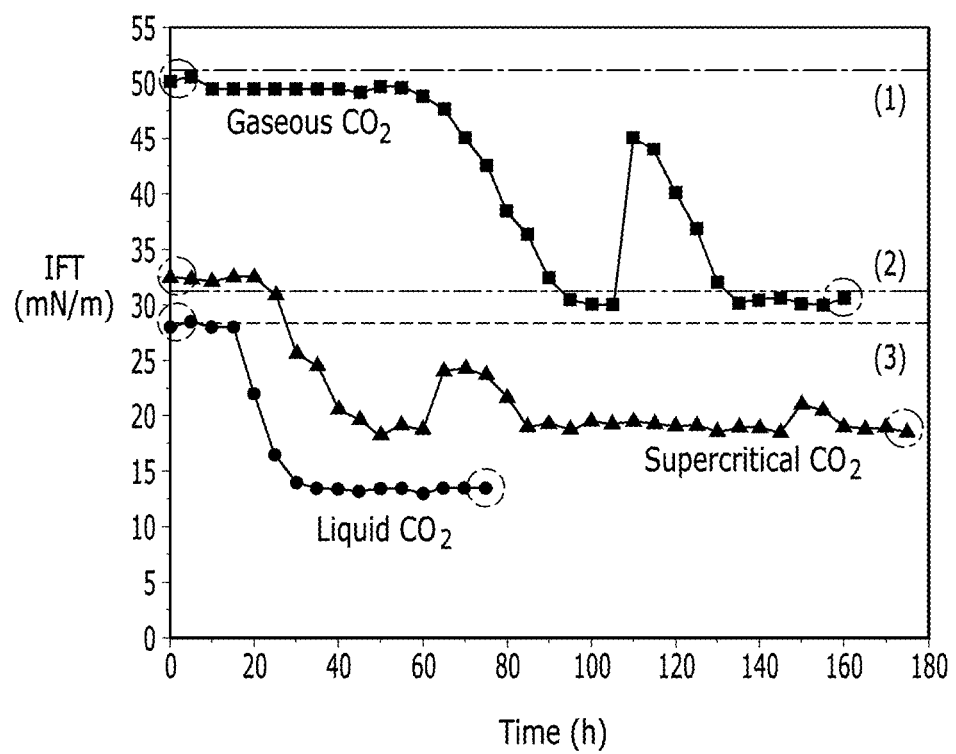
FIG. 4A is a graph that shows measurement of interfacial tension variation between carbon dioxide in gas, liquid, and supercritical states and water.
Figure 4B:
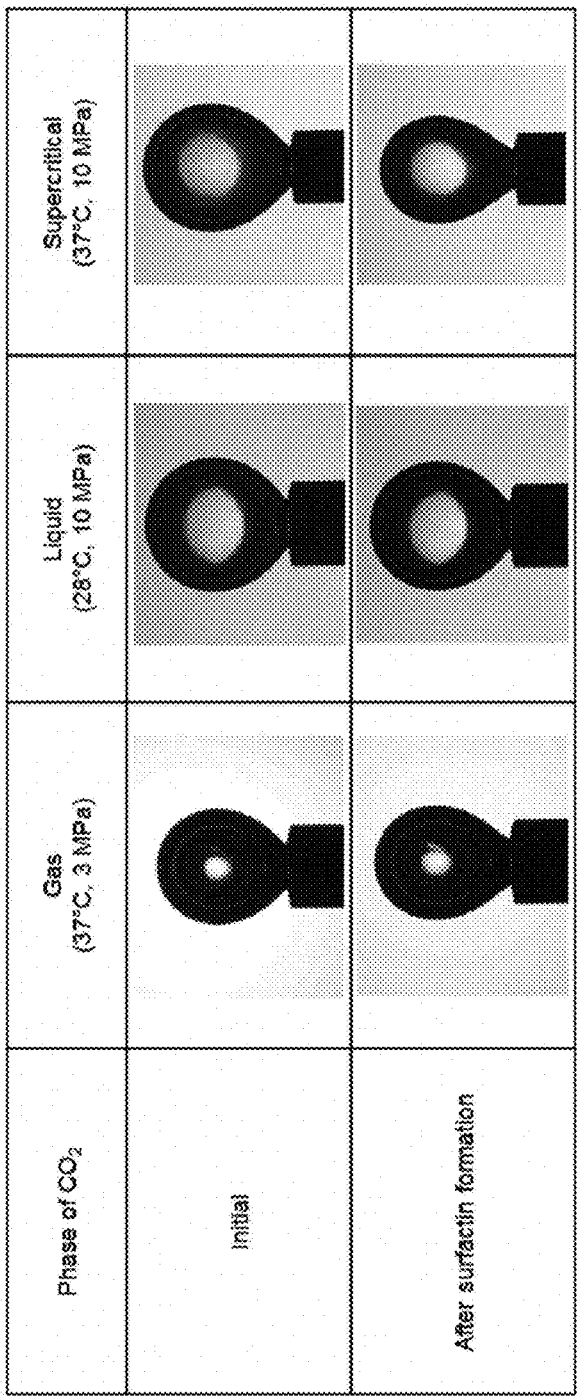
FIG. 4B shows a photographed image under a condition that corresponds to portions marked by dotted circles in FIG. 4A.

FIG. 4A is a graph that shows measurement of interfacial tension variation between carbon dioxide in gas, liquid, and supercritical states and water, and FIG. 4B shows a photographed image under a condition that corresponds to portions marked by dotted circles in FIG. 4A. Specifically, FIG. 4B shows photographed images of shapes of carbon dioxide in the gas, liquid, and supercritical states before and after generation of the biosurfactant.

In FIG. 4A, the dotted line (1) (gas state), the dotted line (2) (supercritical state), and the dotted line (3) (liquid state) indicate interfacial tension between carbon dioxide and water, respectively shown in existing documents.

Although it is not specifically described, generation of surfactin by *Bacillus subtilis* was determined through FT-IR spectrum analysis.

Referring to FIG. 4A and FIG. 4B, due to generation of the biosurfactant, carbon dioxide in the gas state, interfacial tension between carbon dioxide in the gas state and water, interfacial tension between carbon dioxide in the liquid state and water, and interfacial tension between carbon dioxide in the supercritical state and water were all decreased.

Interfacial tension between carbon dioxide in the gas state (37° C. and 3 MPa) and water was reduced to about 13 mN/m from about 49.5 mN/m, which is about a 39% decrease, interfacial tension between carbon dioxide in the liquid state (28° C. and 10 MPa) and water was reduced to about 13 mN/m from about 28.5 mN/m, which is about a 54% decrease, and interfacial tension between carbon dioxide in the supercritical state (37° C. and 10 MPa) and water was reduced to about 18.5 mN/m from about 32.5 mN/m, which is about a 43% decrease.

Although it is not specifically described, such a decrease of interfacial tension can be determined through variation in the shape of the interfacial curves by a known Laplace equation from the images of FIG. 4B.

Figure 5A:
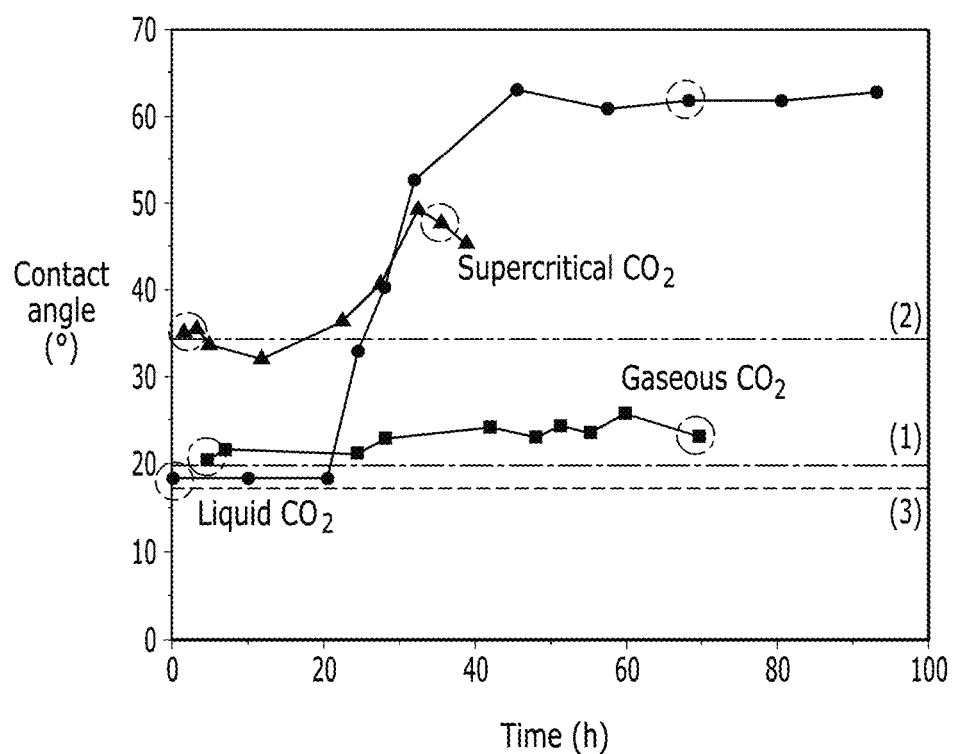
FIG. 5A is a graph that shows contact angle variation between carbon dioxide in the gas state, the liquid state, and the supercritical state and a quartz plate according to generation of the biosurfactant.
Figure 5B:
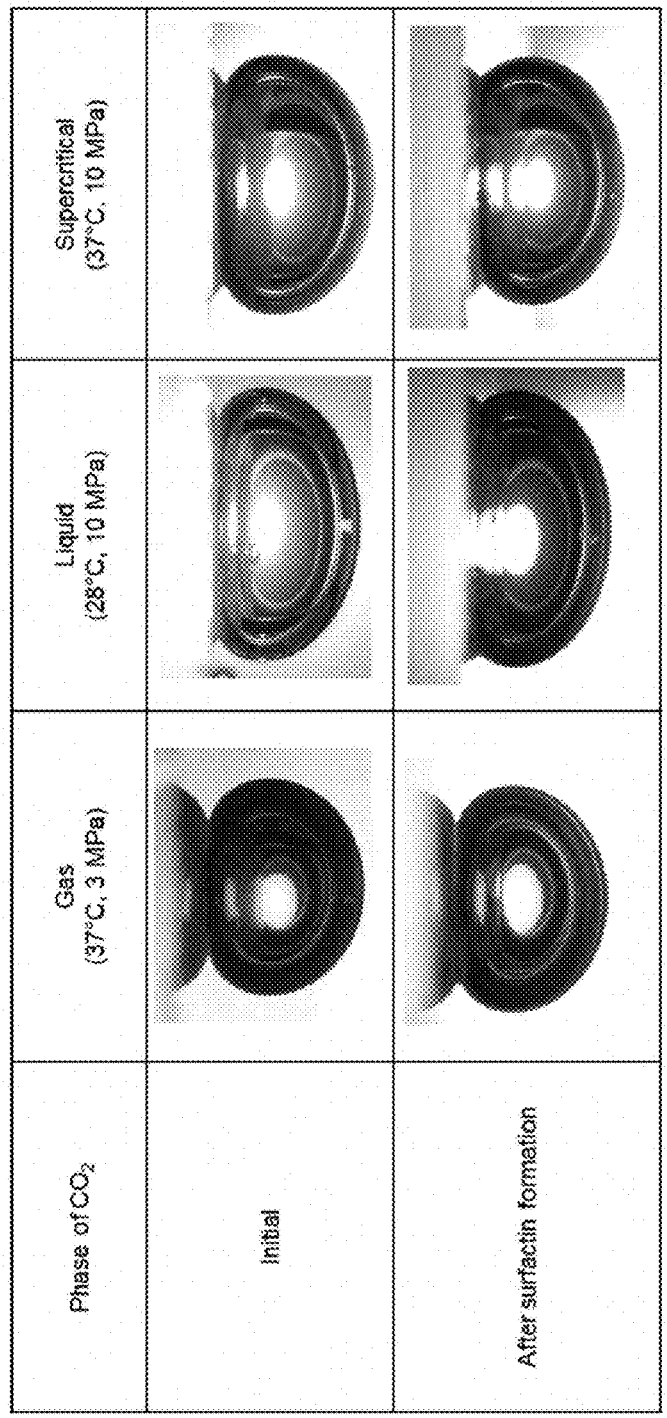
FIG. 5B shows photographed images of carbon dioxide and a quartz plate under conditions that correspond to portions marked by the dotted circles in FIG. 5A.

FIG. 5A is a graph that shows contact angle variation between carbon dioxide in the gas state, the liquid state, and the supercritical state and a quartz plate according to generation of the biosurfactant, and FIG. 5B shows photographed images of carbon dioxide and a quartz plate under conditions that correspond to portions marked by the dotted circles in FIG. 5A. Specifically, FIG. 5B shows photographed images of shapes of carbon dioxide in the liquid state, the gas state, and the supercritical state on the quartz plate before and after generation of the biosurfactant.

In FIG. 5A, the dotted line (1) (gas state), the dotted line (2) (supercritical state), and the dotted line (3) (liquid state) indicate contact angles between carbon dioxide and the quartz plate, respectively shown in existing documents.

Although it is not specifically described, generation of surfactin by *Bacillus subtilis* was determined through FT-IR spectrum analysis.

A contact angle between carbon dioxide in the gas state (37° C. and 3 MPa) and the quartz plate was increased to about 23.2° from 20.5°, which is an increase of about 1.16 times, a contact angle between carbon dioxide in the liquid state (28° C. and 10 MPa) and the quartz plate was increased to about 61.8° from about 18.4°, which is an increase of about 3.36 times, and a contact angle between carbon dioxide in the supercritical state (37° C. and 10 MPa) and the quartz plate was increased to about 47.7° from 35.5°, which is an increase of about 1.34 times.

Referring to FIG. 5B, it can be determined that all the contact angles between carbon dioxide and the quartz plates were increased after generation of surfactin in all the conditions of the gas state, the liquid state, and the supercritical state.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A geological storage system of carbon dioxide comprising:
    an injection pipe that extends to a carbon storage reservoir that includes a plurality of rock grains and brine, from the ground surface, and supplies an injection material that includes carbon dioxide ($CO_2$) to the carbon storage reservoir;
    a plurality of pores that are disposed between the plurality of rock grains; and
    a storage structure that is connected with a part of the plurality of pores and where the carbon dioxide reaches through the plurality of pores and then stored,
    wherein the plurality of pores and the storage structure are filled with the brine, and
    the carbon dioxide is separated from the brine by being surrounded by biosurfactants produced by microorganisms included in the injection material.

2. The geological storage system of carbon dioxide of claim 1, wherein the carbon dioxide is in a gas state, a liquid state, or a supercritical state.

3. The geological storage system of carbon dioxide of claim 1, wherein the microorganism is *Bacillus subtilis*, and the biosurfactant is surfactin.

4. The geological storage system of carbon dioxide of claim 1, wherein the biosurfactants form a micelle structure, and the carbon dioxide is trapped in the micelle structure.

5. The geological storage system of carbon dioxide of claim 1, wherein cap rocks are disposed in upper and lower portions of the carbon storage reservoir.

6. A method for geologically storing carbon dioxide, comprising:
    supplying an injection material that includes carbon dioxide ($CO_2$), microorganisms, and a bacterial growth medium through an injection pipe that extends to a carbon storage reservoir that includes a plurality of rock grains and brine, from the ground surface;
    forming a micelle structure by biosurfactants produced by the microorganisms, and forming a storage material by trapping the carbon dioxide in the micelle structure;
    moving the storage material through a plurality of pores that are disposed between the plurality of rock grains and filled with the brine; and
    storing the storage material by moving the storage material to a storage structure that is partially connected with the plurality of pores and filled with the brine.

7. The method for geologically storing carbon dioxide of claim 6, comprising, before the supply of the injection material to the carbon storage reservoir, converting a phase of the carbon dioxide to a liquid state or a supercritical state by using a phase conversion device.

8. The method for geologically storing carbon dioxide of claim 7, wherein the phase of the carbon dioxide is determined corresponding to a temperature and a pressure environment of the carbon storage reservoir.

9. The method for geologically storing carbon dioxide of claim 6, wherein the microorganism is *Bacillus subtilis*, and the biosurfactant is surfactin.

10. The method for geologically storing carbon dioxide of claim 6, wherein, in the supplying of the injection material to the carbon storage reservoir, an injection temperature, an injection pressure, and an injection amount of the injection material are controlled.

* * * * *